United States Patent [19]

Pilgram et al.

[11] 4,134,752
[45] Jan. 16, 1979

[54] PLANT GROWTH REGULATORS

[75] Inventors: Kurt H. G. Pilgram; Earl K. Jackson; Willy D. Kollmeyer, all of Modesto, Calif.

[73] Assignee: Shell Oil Company, Houston, Tex.

[21] Appl. No.: 531,260

[22] Filed: Dec. 10, 1974

Related U.S. Application Data

[60] Division of Ser. No. 253,356, May 15, 1972, Pat. No. 3,876,678, which is a continuation-in-part of Ser. No. 162,709, Jul. 14, 1971, abandoned.

[51] Int. Cl.$^2$ .......................... A01N 9/14; A01N 5/00
[52] U.S. Cl. .......................................... 71/103; 71/72; 71/76; 71/77
[58] Field of Search ...................... 71/103, 72, 76, 77

[56] References Cited

U.S. PATENT DOCUMENTS

| | | | |
|---|---|---|---|
| 2,654,667 | 10/1953 | Goodhue et al. | 71/103 |
| 2,802,035 | 8/1967 | Fincke | 71/103 |
| 3,210,339 | 10/1965 | Schwarze et al. | 71/86 |
| 3,419,620 | 12/1968 | Becher et al. | 71/86 |
| 3,463,803 | 8/1969 | Aichenegg | 71/103 |

OTHER PUBLICATIONS

Cooke et al., "2-Haloethanephosphonic Acids as, etc;" (1968) Nature 218, pp. 974–975 (1968).
Sato et al., "Oxidation of Episulfides, etc.;" (1970) CA 73, No. 120488u (1970).
Etlis et al. "Chlorination of Some Alkene Sulfides," (1965) CA 63, p. 479 (1965).

*Primary Examiner*—Catherine L Mills

[57] ABSTRACT

A method of regulating and/or modifying the growth of plants by applying to the plant locus, certain beta-substituted ethanesulfinic acids, and oxygen esters thereof, is described as well as plant growth regulant formulations containing them. Some of the compounds described for use in the method of the invention are novel.

7 Claims, No Drawings

PLANT GROWTH REGULATORS

This is a division of application Ser. No. 253,356, filed May 15, 1972, now U.S. Pat. No. 3,876,678, which is a continuation-in-part of Ser. No. 162,709, filed July 14, 1971 now abandoned.

BACKGROUND OF THE INVENTION

1. Field of the Invention

This invention relates to the discovery that beta-chloro- and beta-bromoethanesulfinic acids and esters can be employed to regulate and/or modify the growth of plants.

2. Description of the Prior Art

Certain of the lower alkyl ethanesulfinate esters which are active in the method of the invention are known compounds. German Pat. No. 2,005,514 discloses the methyl, ethyl and isopropyl esters of 2-chloro- or bromoethanesulfinic acid as anti-cancer agents. The preparation of the tertiary butyl ester of 2-chloroethanesulfinic acid is disclosed in V. S. Etlis et al., *Journal General Chemistry U.S.S.R* 35, 472-75 (1965). Also, one of the free sulfinic acids useful in the method of the invention, 2-chloroethanesulfinic acid, is disclosed in A. I. Titov and A. N. Baryshnikova, *Akad. Nauk., SSR,* 157, 681 (1964) and H. Distler, *Angew. Chem. Internat. Ed.* 4, 300 (1965). However, no reference is known which discloses or suggests the plant growth regulant properties of these known compounds or the class of compounds as a whole which have been found to be active in the process of the invention. Other related art is G. Hesse et al., *Chem. Ber.* 90, 2106 (1957) which discloses the barium salt of 2-hydroxyethanesulfinic acid and U.S. Pat. No. 2,412,909 which discloses a general reaction wherein unspecified alkyl or substituted alkyl sulfinyl halides may be reacted with alcohols, phenols, etc. to form products which are useful as bleaching agents, dyes, plasticizers and a variety of other uses, but not including plant growth regulators.

SUMMARY OF THE INVENTION

Surprisingly, it has now been discovered that certain ethanesulfinic acids and oxygen esters thereof wherein the beta carbon atom of the ethylene moiety is substituted with bromine or chlorine, can be employed to regulate and/or modify the growth of plants. Depending on variables such as the species of plant treated, plant maturity at time of treatment, the quantity and concentration of growth regulant used, the specific compound used, and the formulation employed, these compounds when applied to the plant locus exhibit a wide variety of useful plant growth regulating properties. Some of the plant growth regulant effects which have been observed include the promotion of early and more uniform fruit ripening and/or abscission, acceleration of leaf abscission, promotion of flowering, stimulation of sprouting of tubers, stimulation of seed germination, destruction of apical dominance in tubers causing lateral buds to sprout, increased formation of root initials on tomato stems, the causation of tomato leaf epinasty and dwarfing of plants. It will be recognized that biological response such as that realized from the process of the instant invention, when utilized as a cultural practice in the agricultural industry, can provide a valuable means of increasing crop productivity while at the same time reducing the labor and expense necessary to produce the crops.

The invention accordingly, is the use of beta-substituted ethanesulfinic acids and esters, hereinbefore described as plant growth regulators and plant growth regulant formulations containing them.

2-Bromoethanesulfinic acid and many of the sulfinic esters useful in the process of the invention are novel. Therefore, the scope of the present invention also encompasses these novel compounds.

DESCRIPTION OF THE PREFERRED EMBODIMENTS

The beta-substituted ethanesulfinic acids and esters found useful to regulate the growth of plants according to the method of this invention are represented by formula I:

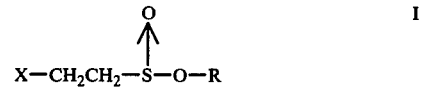

wherein X represents bromine, chlorine or alkoxy of up to 3 carbon atoms; R is hydrogen, alkyl of up to 20 carbon atoms, aryl of up to 10 carbon atoms, alkenyl of up to 8 carbon atoms, alkynyl of up to 4 carbon atoms or ZR' wherein Z is alkylene of up to 4 carbon atoms and R' is alkylthio of up to 3 carbon atoms or alkoxy of up to 4 carbon atoms, or hydroxy; if X is chlorine, R' also represents $ZR^2$ wherein Z is as defined above and $R^2$ is a beta-chloroethanesulfinyloxy moiety. Any of these alkyl groups may be of either straight chain or branched chain configuration.

Exemplary species of the class of the invention include:
2-methoxyethyl 2-chloroethanesulfinate
propyl 2-bromoethanesulfinate 2-bromoethanesulfinic acid
phenyl 2-bromoethanesulfinate
naphthyl 2-chloroethanesulfinate
2-(ethylthio)ethyl 2-bromoethanesulfinate
2-methoxypropyl 2-bromoethanesulfinate
2-butoxypropyl 2-chloroethanesulfinate
propynyl 2-bromoethanesulfinate Many of the compounds active in the method of the invention have not previously been known in the art. Thus, the following are considered to be novel compounds and form a preferred aspect of this invention (symbols refer to formula I, above):

I. Sulfinic Acids

The compound wherein X is bromine and R is hydrogen.

II. Sulfinate Esters

Compounds wherein X is chlorine or bromine, R is alkyl of from 6 to 20 carbon atoms, alkynyl of up to 4 carbon atoms, alkenyl of up to 8 carbon atoms, aryl of up to 10 carbon atoms, or ZR wherein Z is alkylene of up to 4 carbon atoms and R is alkylthio of up to 3 carbon atoms or alkoxy of up to 4 carbon atoms or hydroxy; Z is as defined above and if X is chlorine R also represents $ZR^2$ wherein $R^2$ represents a beta-chloroethanesulfinyloxy moiety.

Of the generic class of compounds useful in the method of this invention, certain species in the sulfinic ester subclass are especially effective in regulating the growth of plants, thus compounds wherein X is chlorine, and R is alkyl of up to 20 carbon atoms or alkenyl of up to 8 carbon atoms make up another preferred aspect of this invention.

Specific examples of this preferred subclass include:
methyl 2-chloroethanesulfinate
amyl 2-chloroethanesulfinate
3-butenyl 2-chloroethanesulfinate
heptyl 2-chloroethanesulfinate
decyl 2-chloroethanesulfinate 3-pentenyl 2-chloroethanesulfinate The compounds of this invention may be applied to seeds prior to planting or to soil surrounding the plants, or to plants, pre-emergence, or at harvest to modify and/or regulate the growth of the plant, or optionally may be applied to stimulate, regulate and/or modify ripening of the harvested portion. For application, compounds of the invention, being either solid or liquid at ambient temperatures, may be formulated using conventional techniques and employing adjuvants and/or modifiers which are known in the agricultural chemical art to provide compositions in the form of wettable powders, dusts, granules, pellets, solutions, emulsifiable concentrates, emulsions and pastes.

Preferred for use on maturing plants or harvested crops are those formulations which furnish the active ingredient to the plant locus in liquid or paste form. These preferred formulations would include wettable powders, solutions, emulsifiable concentrates, emulsions and pastes. Wettable powders are water-dispersible compositions containing the active ingredient in proportions ranging from 10 to 90% of the total composition, and an inert solid carrier such as one of the natural clays or a synthetic mineral filler derived from silica and silicate. Optionally, such wettable powder may also contain 3-10% of a dispersing agent and where necessary 0-10% of stabilizer(s) and/or other additives such as penetrants or stickers. The term "solution" includes both aqueous and non-aqueous solutions of the compounds of the invention. Certain of the compounds of the invention are soluble in aqueous media and can be formulated and applied in aqueous solution at concentrations up to 10%. Other compounds of the invention are less or sparingly soluble in water and exhibit proportionally higher solubility in non-aqueous solution and may be formulated and applied at concentrations of up to 50%. The emulsifiable concentrates contemplated for use in the method of the invention usually contain, in addition to the solvent and, when necessary, co-solvent, 10-50% w/v active ingredient, 2-20% w/v emulsifiers and 0-20% appropriate additives such as stabilizers, penetrants and corrosion inhibitors. Pastes are compounded so as to obtain a stable flowable product and usually contain 10-60% active ingredient, 2-20% of appropriate additives, and, as carrier, water or an organic liquid in which the plant growth regulator is substantially insoluble.

For season long treatment, i.e., application at time of planting or application to plants in early stages of growth, or for other specialized applications, solid formulations of the compounds of the invention may be desired. Suitable solid formulations would include dusts, granules and pellets. Dusts usually have a composition similar to that of a wettable powder but without a dispersant, and normally contain ½ to 10% of plant growth regulator. Dust may also be formulated as concentrates which are then usually diluted further with solid carrier in suitable blending equipment prior to use in the field. Granules and pellets are usually prepared to have a size between 10 and 100 BS mesh, and may be manufactured by agglomeration compaction or impregnation techniques. Generally, granules will contain ½-25% of plant growth regulator plus additives such as stabilizers, slow-release modifiers, binding agents, etc. Except where indicated otherwise, all percentages given in this and the preceeding paragraph are percentages by weight.

To achieve the plant growth regulating and modifying effects hereinbefore described, formulations of the compounds of the invention may be applied directly to the plant fruit or as foliar-soil treatments, seed treatments, foliar treatments or soil treatments. The rate of application will be dependent on the type of application technique utilized as well as other factors such as the particular active agent used, the particular formulation employed, the particular species of plants involved, the maturity stage of the plant, the types of effect desired and the local conditions; for example, temperature, humidity, soil moisture, chemical make-up of the soil and the like. In general, for plants in agronomic environment, rates from 0.05 to 20 pounds per acre can be used to stimulate and/or modify plant growth. However, the preferred rates for most uses range between 0.1 and 5.0 pounds per acre. For application to the plant fruit or harvested crop, the rate of application may range between 1 and 20,000 ppm (parts per million based on total fruit weight) with rates of from 100 to 4,000 ppm being preferred.

The compounds of this invention as described by formula I, above, may be prepared by the following synthesis techniques.

I. Sulfinic Acids (compounds wherein R is hydrogen)

The beta-substituted ethanesulfinic acids of this invention may be prepared by the reaction of a beta-substituted ethanesulfinyl chloride of the formula II

wherein X is bromine or chlorine, with water. This reaction is suitably carried out in an inert organic solvent such as ether and the by-product hydrogen chloride, which is generated in the reaction, is effectively removed by sparging the reaction mixture with nitrogen during the reaction period.

The beta-substituted ethanesulfinyl chloride described by formula II can be prepared by oxidative chlorination of the corresponding bis(beta-substituted-ethyl) disulfide wherein the beta substituents of the disulfide are the same as the beta substituent on the sulfinyl chloride. This technique, which utilizes a general method described by I. B. Douglass and R. V. Norton, *Journal of Organic Chemistry*, 33, 2104 (1968) for conversion of certain disulfides to sulfinyl chlorides, involves the reaction of chlorine gas with the bis(beta-substituted-ethyl) disulfide in glacial acetic acid. The bis(beta-substituted-ethyl) disulfide reactants utilized in the synthesis technique described above are known in the art, e.g. see G. Y. Epshtein et al, *J. Gen. Chem. USSR*, 34, 1961 (1964); see also, Fuson et al., *J. Org. Chem.* 11, 491 (1946).

II. Sulfinate Esters

All of the beta-substituted ethanesulfinate esters described by formula I above, except compounds wherein R is aryl, may be prepared by the reaction of a beta-substituted ethanesulfinyl chloride of the formula II with a hydroxy compound of formula III as illustrated by equation I, below

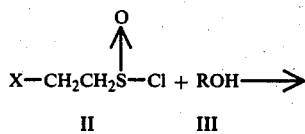

Equation I

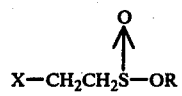

wherein X is as defined in formula I above and R represents all the moieties defined for R in formula I above except aryl. This reaction is suitably carried out in an inert solvent such as ether and at reaction temperatures less than ambient. Due to the highly reactive nature of the sulfinyl chloride, the reaction is preferably carried out under an inert (nitrogen) atmosphere.

Beta-substituted ethanesulfinate esters of this invention wherein R is aryl may be prepared by the reaction of a thallium(I) salt of a hydroxy compound of formula VI with a beta-substituted ethanesulfinyl chloride of formula II as illustrated by equation II below. This reaction is suitably performed in an inert solvent such as ether or benzene under and inert atmosphere.

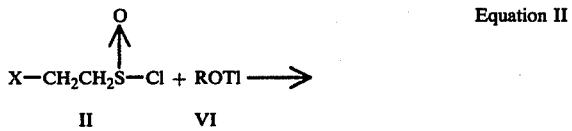

Equation II

The products of this reaction are most suitably purified by molecular distillation.

The following examples are illustrative of methods of preparing the compounds of this invention and their use in regulating plant growth. In these examples, parts by weight (w) and parts by volume (v) bear the same relation as the kilogram to the liter and all temperatures are in degrees centigrade. In all cases, the structures of the compounds prepared were confirmed by infrared spectra, nuclear magnetic resonance spectra and elemental analyses.

EXAMPLE I

2-Chloroethanesulfinic Acid

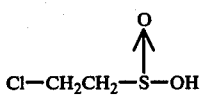

Bis(2-chloroethyl) disulfide was oxidatively chlorinated according to the general method disclosed in I. B. Douglass and R. V. Norton, *Journal of Organic Chemistry*, 33, 2104 (1968) as follows: Bis(2-chloroethyl) disulfide (38.0 w) was charged into a reaction vessel containing glacial acetic acid (24.0 w) and the mixture was cooled to 10°. Chlorine gas was introduced to the cooled solution at a rate such that the reaction mixture was maintained at about 10°. The chlorine addition was continued until the deep orange color of the reaction mixture disappeared. The solution was then distilled at reduced pressure to yield a clear liquid, 2-chloroethanesulfinyl chloride (50.4 w), boiling point 82–82° under reduced pressure (12 torr).

Water (3.6 w) was added in one portion to a solution of 2-chloroethanesulfinyl chloride (29.4 w) in ether (250 v). The reaction mixture was held for one hour at ambient temperatures during which time a vigorous stream of nitrogen was bubbled through the mixture. Upon completion of the hold period, the reaction solution was concentrated by distillation in a vacuum to give a colorless liquid (26.4 w). Further purification of this liquid by molecular distillation at 75° and $1 \times 10^{-4}$ torr provided a colorless viscous oil, 2-chloroethanesulfinic acid (14.5 w).

EXAMPLE II 2-(Ethyl)hexyl 2-chloroethanesulfinate

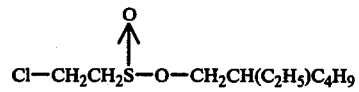

A stirred portion of 2-chloroethanesulfinyl chloride (16.2 w) prepared as in Example I, cooled to −15 to −30° C, was treated dropwise with 2-ethylhexanol (13.0 w) under a nitrogen atmosphere. Upon completion of the addition the external cooling was removed and the reaction mixture was allowed to stand for 16 hours at ambient temperature. Distillation through a 20 cm Vigreux column afforded a clear white liquid, (2-ethyl)-hexyl 2-chloroethanesulfinate (14.7 w) boiling at 110 to 112° under reduced pressure (0.3 torr).

EXAMPLE III

Butyl 2-chloroethanesulfinate

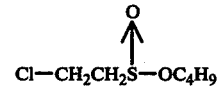

2-Chloroethanesulfinyl chloride (16.2 w), prepared as in Example I was dissolved in dry ether (130 v) and the solution was cooled to −15°. Normal butanol was added dropwise under a nitrogen atmosphere to the cooled solution. Upon completion of the addition period the reaction mixture was allowed to warm to ambient temperatures and the solvent was removed by distillation in a vacuum to yield a colorless liquid, butyl 2-chloroethanesulfinate (18.5 w).

EXAMPLE IV 2-(Chloroethanesulfinyloxy)ethyl 2-chloroethanesulfinate

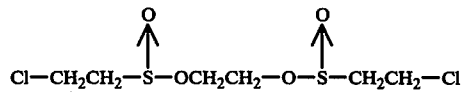

Ethyl glycol (6.2) was added dropwise under a nitrogen atmosphere to a stirred solution of 2-chloroethanesulfinyl chloride (14.7 w), prepared as in Example I, in dry ether (40 v). During the addition period the temperature of the reaction was controlled at −20° by external cooling. Upon completion of the addition, the reaction mixture was warmed to ambient temperature and the solvent was removed by distillation in a vacuum. Examination of the residue by gas-liquid chromatography revealed more than one major component. The residue was then redissolved in dry ether (200 v) and further treated with 2-chloroethanesulfinyl chloride (14.7 w) as above. Using the same procedure as above an oily residue was obtained which after purification in a wiped film molecular still yielded a colorless liquid, 2-(chloroethanesulfinyloxy)ethyl 2-chloroethanesulfinate (8.5 w) boiling at 110–115° under reduced pressure (1 × 10$^{-4}$ torr).

EXAMPLE V 2-(Ethylthio)ethyl 2-chloroethanesulfinate

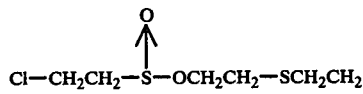

A solution of ethyl 2-hydroxyethyl sulfide (10.6 w) in dry ether (50 v) was slowly added to 2-chloroethanesulfinyl chloride (14.7 w) in dry ether (200 v) maintained at about −10° under a nitrogen atmosphere. Upon warming to ambient temperature, the reaction mixture was evaporated under reduced pressure. The residual oil was passed through a wiped film molecular still to yield 2-(ethylthio)ethyl 2-chloroethanesulfinate (15.4 w) boiling at 95–100° under reduced pressure (1 × 10$^{-4}$ torr).

EXAMPLE VI

Phenyl 2-chloroethanesulfinate

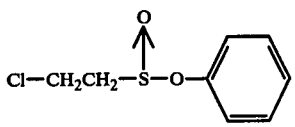

A suspension of thallium (I) phenoxide (28.6 w) in dry ether (100 v) was rapidly treated with 2-chloroethanesulfinyl chloride, prepared as in Example I. The slurry was vigorously stirred for 1 hour at ambient temperature with exclusion of moisture. Removal of thallium(I) chloride by filtration and evaporation of the etheral filtrate solution gave an oil. The oil was then subjected to molecular distillation in a wiped-film apparatus at 70–75° (1 × 10$^{-4}$ torr) to give phenyl 2-chloroethanesulfinate (122 w) as a mobile liquid.

EXAMPLE VII

Following procedures similar to those given in previous examples, the following other species of the compounds of the invention were prepared (symbols refer to formula I).

Table I

| X | R | Melting Point, °C or Boiling Point, °C (torr) |
|---|---|---|
| Cl | —CH$_3$ | 74 – 76 (4.0) |
| Cl | —CH$_2$CH$_3$ | 62 – 64 (0.75) |
| Cl | —CH(CH$_3$)$_2$ | 64 – 67 (0.15) |
| Cl | —CH$_2$(CH$_2$)$_4$CH$_3$ | 55 – 60 (1 × 10$^{-4}$) |
| Cl | —CH$_2$(CH$_2$)$_6$CH$_3$ | 116 – 117 (0.25) |
| Cl | —CH$_2$(CH)$_{10}$CH$_3$ | not determined |
| Cl | —CH$_2$(CH$_2$)$_{14}$CH$_3$ | 27 – 29 |
| Cl | —CH$_2$(CH$_2$)$_{18}$CH$_3$ | 48 – 49 |
| Cl | —CH$_2$CH=CH$_2$ | 70 – 75 (1 × 10$^{-4}$) |
| Cl | —CH$_2$C≡CH | 80 – 85 (1 × 10$^{-4}$) |
| Cl | —CH$_2$CH$_2$O(CH$_2$)$_3$CH$_3$ | 70 – 75 (1 × 10$^{-4}$) |
| Cl | —CH$_2$CH$_2$—OH | not determined |
| Br | —CH$_3$ | 58 – 60 (0.30) |
| Br | —CH$_2$(CH$_2$)$_4$CH$_3$ | 85 – 90 (1 × 10$^{-4}$) |

EXAMPLE VIII

Fruit Abscission

Washington Navel oranges were harvested in a manner such that the fruit was still attached to 4 inches of stem having two (2) clusters of leaves. The pull force required to cause abscission of the fruit from the cut stems was 14–16 pounds. The harvested oranges were then segregated into groups of five (5) oranges each (stems and leaves still attached) and the segregated groups were sprayed to dripping with several concentrations of methyl 2-chloroethanesulfinate in aqueous solution. A water treatment was used as a control. Some oranges began to drop off the stems two days after treatment with the higher concentrations of methyl 2-chloroethanesulfinate while the fruit in the control groups remained attached to the stems. The rates of application as well as the observations of the fruit abscission occurring seven (7) days after treatment for both the treatment groups and the control groups are recorded in Table II below.

Table II

| Treatment | Concentration (ppm) | Number of Oranges Separated From Stems |
|---|---|---|
| Water | — | 2 |
| methyl 2-chloroethanesulfinate | 4000 | 5 |
| methyl 2-chloroethanesulfinate | 2000 | 5 |
| methyl 2-chloroethanesulfinate | 1000 | 3 |

EXAMPLE IX

Fruit Ripening

Green field picked tomatoes were randomized and segregated into a treatment group and a control group. The tomatoes in the treatment group were painted with a 1000 ppm aqueous solution of methyl 2-chloroethanesulfinate containing 0.2% Tronic as a surfactant. The tomatoes in the control group were painted in the same manner with the base solution. Eighteen days after treatment all the tomatoes in the treatment group were fully red whereas with the control group only two of the tomatoes had begun turning red twenty days after treatment.

EXAMPLE X

Stimulation of Seed Germination

Under normal conditions experience has shown that only 40% of cocklebur seeds will germinate. Fifty cocklebur seeds were soaked for one hour in either water or methyl 2-chloroethanesulfinate at 1000 ppm w/v water. All seeds were planted and allowed to germinate over a ten day period. Treatment with methyl 2-chloroethanesulfinate increased seed germination by 25% over the controls.

EXAMPLE XI Stimulation of Tuber Sprouting

Twenty-four yellow nutsedge tubers were soaked in a 100 ppm aqueous solution of methyl 2-chloroethanesulfinate for ten minutes, blotted dry and sealed in a bottle. A like number of tubers were soaked in water and sealed according to the same procedure. Six days after treatment all (100%) of the treatment had sprouted whereas only 81% of the control tubers had sprouted. Also, the number of shoots formed per tuber increased from 1.3 for the control group to 1.6 for the treatment group. Treatment with methyl 2-chloroethanesulfinate, therefore, stimulated sprouting and destroyed the normal dominance of the apical bud thus allowing lateral buds to sprout.

EXAMPLE XII

Leaf Abscission

Individual branches of Washington Navel orange trees were treated with aqueous solutions of several of the compounds of the invention. Each of the compounds tested was made up as a 200 ppm solution in water containing 0.2% Tronic as surfactant. A total of 100 ml of each of the resulting solutions was applied as a foliar spray to a single branch of Washington Navel orange trees. Seven days after treatment some of the leaves on the treated branches became stiff, although still green, and began to fall from the trees. Observations of the defoliation caused by each chemical six weeks after treatment are recorded in the following table. Evaluation of defoliation was based on four classifications: 1 to 10%, 11 to 30%, 31 to 60% and 61 to 100% abscission of the leaves originally present.

Table III

| Compound Tested | Percent Abscission |
|---|---|
| methyl 2-chloroethanesulfinate | 1 to 10 |
| ethyl 2-chloroethanesulfinate | 1 to 10 |
| isopropyl 2-chloroethanesulfinate | 1 to 10 |
| hexyl 2-chloroethanesulfinate | 11 to 30 |
| octyl 2-chloroethanesulfinate | 1 to 10 |

None of the leaves dropped from the untreated control branches or those sprayed with the base solution.

EXAMPLE XIII

Fruit Ripening

A second experiment was conducted to evaluate the efficacy of the compounds of the invention in ripening green harvested tomatoes. In this experiment green mature tomatoes were picked from plants grown in a greenhouse and randomly segregated into groups of ten each for treatment. The treatment chemicals were made up in water/acetone solutions at a concentration of 1000 ppm and each group of tomatoes was soaked for one hour in one of the solutions containing a treatment chemical or in the base solution without chemical. Each tomato in each group was evaluated daily by the following color rating: green (0 points), breaker (1 point), ⅓ orange (2 points), full orange (3 points) and red ripe (4 points). When all tomatoes in a group are fully ripe the score will be 40 points thus equaling 100%. The results are listed in Table IV below.

Table IV

| Treatment | Percent Ripeness - Days After Treatment | | | | | | | | | | |
|---|---|---|---|---|---|---|---|---|---|---|---|
| | 1 | 2 | 3 | 4 | 5 | 6 | 7 | 8 | 9 | 10 | 14 |
| Control | 3 | 3 | 8 | 18 | 28 | 38 | 63 | 68 | 80 | 93 | 98 |
| 2-chloroethanesulfinic acid | 13 | 15 | 30 | 48 | 55 | 68 | 75 | 78 | 85 | 90 | 95 |
| ethyl 2-chloroethanesulfinate | 10 | 10 | 30 | 38 | 45 | 53 | 58 | 73 | 83 | 83 | 93 |
| 2-propynyl 2-chloroethanesulfinate | 8 | 25 | 45 | 55 | 60 | 68 | 78 | 80 | 83 | 90 | 98 |
| isopropyl 2-chloroethanesulfinate | 8 | 10 | 28 | 38 | 53 | 60 | 65 | 68 | 73 | 75 | 95 |
| allyl 2-chloroethanesulfinate | 8 | 11 | 22 | 28 | 42 | 58 | 67 | 72 | 80 | 86 | 95 |
| octyl 2-chloroethanesulfinate | 8 | 8 | 15 | 25 | 35 | 48 | 55 | 58 | 65 | 83 | 98 |
| 2-butoxyethyl 2-chloroethanesulfinate | 6 | 11 | 19 | 36 | 56 | 64 | 75 | 78 | 80 | 92 | 100 |
| 2-(chloroethanesulfinyloxy)-ethyl 2-chloroethanesulfinate | 5 | 10 | 25 | 43 | 48 | 65 | 75 | 75 | 80 | 85 | 100 |
| butyl 2-chloroethanesulfinate | 5 | 15 | 23 | 40 | 58 | 70 | 78 | 78 | 80 | 83 | 95 |
| hexyl 2-chloroethanesulfinate | 5 | 8 | 33 | 43 | 55 | 63 | 78 | 85 | 93 | 93 | 100 |
| 2-ethyl hexyl 2-chloroethanesulfinate | 5 | 5 | 18 | 23 | 33 | 55 | 68 | 70 | 78 | 88 | 98 |
| 2-(ethylthio)ethyl 2-chloroethanesulfinate | 5 | 5 | 10 | 18 | 35 | 43 | 58 | 63 | 65 | 70 | 90 |
| methyl 2-chloroethanesulfinate | 3 | 5 | 10 | 18 | 33 | 38 | 48 | 50 | 63 | 70 | 88 |
| eicosyl 2-chloroethanesulfinate | 3 | 8 | 20 | 30 | 33 | 50 | 58 | 70 | 80 | 85 | 93 |

As indicated in the table above, the compounds of the invention in this test were most effective in stimulating early ripening of the test plants. This effect is illustrated by the relative ripeness values at 5 days after treatment.

EXAMPLE XIV

Fruit Ripening

This test was conducted to evaluate the efficacy of the compounds of the invention as ripening agents for mature fruit prior to harvest, i.e., fruit still attached to the growing plant. Individual clusters of mature green cherry tomatoes grown in a greenhouse were treated with the compounds of the invention while still on the vine. For treatment, the test compounds were made up in a acetone/water solution at a concentration of 1000 ppm and each test solution was applied thoroughly to a different set of 4 clusters of tomatoes, each cluster having 4 to 6 mature tomatoes. One set of tomatoes was treated with the base solution for control purposes. The results are listed in Table V below.

Table V

| Treatment | Red Tomatoes - Days After Treatment | | | | |
|---|---|---|---|---|---|
| | 5 | 8 | 13 | 16 | 19 |
| Control | 0 | 0 | 5 | 15 | 30 |
| methyl 2-methoxyethanesulfinate | 6 | 17 | 39 | 56 | 73 |
| allyl 2-chloroethanesulfinate | 0 | 0 | 41 | 47 | 82 |
| cetyl 2-chloroethanesulfinate | 0 | 0 | 14 | 43 | 64 |
| methyl 2-chloroethanesulfinate | 0 | 0 | 15 | 34 | 54 |
| lauryl 2-chloroethanesulfinate | 0 | 0 | 10 | 27 | 58 |
| eicosyl 2-chloroethanesulfinate | 0 | 0 | 11 | 22 | 58 |

EXAMPLE XV

Fruit Ripening

Picked, green, untreated bananas were separated and randomly grouped for treatment. The treatment consisted of spraying each of the different treatment groups, one untreated group being retained as a control, with a 1000 ppm aqueous solution of one of the following compounds of the invention: methyl 2-chloroethanesulfinate and hexyl 2-chloroethanesulfinate. In all cases the treated bananas turned completely yellow two to five days before the untreated bananas.

EXAMPLE XVI

Leaf Epinasty

Leaf epinasty is a hormonal response which occurs in plants wherein the upper side of the leaf stalk grows more rapidly than the lower side causing the leaf to bend downward. To evaluate for leaf epinasty response, three and six week old tomato plants were randomly segregated into groups of three plants each and each group was sprayed with a different compound of the invention at a concentration of 2000 ppm in aqueous solution containing 0.2% Tronic surfactant. One unsprayed group was retained for control. The plants under test were evaluated on a periodic basis throughout the test for epinasty response; the observations of leaf epinasty which had occurred thirteen days after treatment are recorded in Table VI below. Evaluation of the degree of leaf epinasty is based on four classifications: no epinasty indicating normal horizontal leaf growth, complete epinasty (90 degrees) indicating that the leaves grew vertically downward around the steam and 30 or 60 degrees epinasty indicating intermediate downward growth of leaves.

Table VI

| Compound Tested | Degree of Leaf Epinasty |
|---|---|
| Control | None |
| ethyl 2-chloroethanesulfinate | 30 |
| isopropyl 2-chloroethanesulfinate | 60 |
| hexyl 2-chloroethanesulfinate | complete |
| octyl 2-chloroethanesulfinate | complete |
| cetyl 2-chloroethanesulfinate | 30 |
| methyl 2-chloroethanesulfinate | 30 |
| lauryl 2-chloroethanesulfinate | complete |
| allyl 2-chloroethanesulfinate | 30 |
| methyl 2-bromoethanesulfinate | 60 |

EXAMPLE XVIII

Leaf Epinasty

A second leaf epinasty test was performed on tomato plants. In this test phenyl 2-chloroethanesulfinate as the test compound was applied as a foliar spray to 3 different tomato plants. Two plants were 37 days old. The older plants were 14 inches high with 10 leaves and the younger third plant was 23 days old. The older plants were 14 inches high with 10 leaves and the younger plants were 10 inches high with 8 leaves. Two ages of plants were included because the older plants usually are more sensitive and give a more rapid hormonal epinasty response. The test compound was dissolved in acetone and diluted to 2500 ppm with water containing 0.4% surfactant (Wilsco Foamspray). A 10 ml volume of the test compound so diluted was applied as a foliar spray to 3 tomato plants. The treated plants were evaluated for epinasty (bending of leaves downward toward the base of the stem) 20 hours after treatment. The test was again evaluated for epinasty as well as phytotoxicity four days after treatment, to determine if the epinasty effects had dissipated. The results of the test including those obtained for the "control" (base solution without test compound) are recorded in Table IX below. The table heading "leaves normal after four days" designates visual observation of whether any effects of epinasty remained 4 days after treatment.

Table IX

| Treatment | Percent of Leaves Showing Epinasty Response | | | | Leaves Normal After 4 Days | Phyto-Toxicity |
|---|---|---|---|---|---|---|
| | No Response | Slight Response | Intermediate Response | Complete Response | | |
| Control | 100 | 0 | 0 | 0 | Yes | None |
| Phenyl 2-chloroethane-sulfinate | 0 | 59 | 8 | 33 | Yes | None |

We claim as our invention:

1. A method for regulating plant growth which comprises applying to the locus to be treated, an effective amount of a compound of formula I:

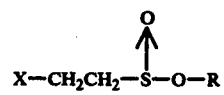

wherein X is bromine or chlorine and R is hydrogen, alkyl of up to 20 carbon atoms, phenyl, alkenyl of up to 8 carbon atoms or alkynyl of up to 4 carbon atoms.

2. The method of claim 1 wherein X is chlorine and R is alkyl of up to 20 carbon atoms a alkenyl of up to 8 carbon atoms.

3. Method of influencing the growth of plants which comprises applying plant growth regulatingly effective amounts of a 2-haloethanesulphinic acid compound of the formula

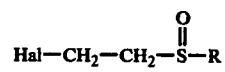

in which
Hal is chlorine or bromine, and
R is hydroxyl or alkoxy of form 1 to 20 carbon atoms.

4. Method as claimed in claim 1 wherein said compound is selected from the group consisting of 2-chloroethanesulphinic acid ethyl ester,
2-chloroethanesulphinic acid isopropyl ester,
2-chloroethanesulphinic acid n-butyl ester,
2-chloroethanesulphinic acid methyl ester,
2-chloroethanesulphinic acid n-pentyl ester,
2-chloroethanesulphinic acid n-octyl ester,
2-chloroethanesulphinic acid hexadecyl ester,
2-chloroethanesulphinic acid 1-propynyl ester,
2-chloroethanesulphinic acid allyl ester, and 2-chloroethanesulfinic acid.

5. Method as claimed in claim 1 wherein said compund is applied at a dosage of from 0.05 to 20 pounds per acre of said area.

6. Method as claimed in claim 1 wherein said dosage is 0.1 to 5 pounds per acre of said area.

7. Method as claimed in claim 1 wherein said compound is applied to stimulate the growth of the plant.

* * * * *